United States Patent [19]

Langley et al.

[11] Patent Number: 5,728,451
[45] Date of Patent: *Mar. 17, 1998

[54] BREATHABLE NON-WOVEN COMPOSITE VIRAL PENETRATION BARRIER FABRIC AND FABRICATION PROCESS

[76] Inventors: John D. Langley, 1904 Forest Dr.; Barry Scott Hinkle, 400 Oak Pl., both of Guntersville, Ala. 35976

[*] Notice: The term of this patent shall not extend beyond the expiration date of Pat. No. 5,409,761.

[21] Appl. No.: 824,449

[22] Filed: Mar. 26, 1997

Related U.S. Application Data

[63] Continuation of Ser. No. 345,602, Nov. 28, 1994, abandoned.

[51] Int. Cl.[6] .................................................. B32B 27/14
[52] U.S. Cl. ............................................. 428/198; 156/290
[58] Field of Search ............................. 428/198; 156/290

[56] References Cited

U.S. PATENT DOCUMENTS

| | | | |
|---|---|---|---|
| 3,634,184 | 1/1972 | Wang | 161/159 |
| 3,770,537 | 11/1973 | Elton | 156/77 |
| 4,041,203 | 8/1977 | Brock et al. | 428/157 |
| 4,308,303 | 12/1981 | Mastroianni et al. | 428/90 |
| 4,379,192 | 4/1983 | Wahlquist et al. | 428/156 |
| 4,539,256 | 9/1985 | Shipman | 428/315.5 |
| 4,828,556 | 5/1989 | Braun et al. | 604/365 |
| 4,867,881 | 9/1989 | Kinzer | 210/490 |
| 5,169,712 | 12/1992 | Tapp | 428/315.5 |
| 5,208,098 | 5/1993 | Stover | 428/284 |
| 5,409,761 | 4/1995 | Langley | 428/198 |

*Primary Examiner*—Helen Lee
*Attorney, Agent, or Firm*—Henry Croskell, Esq.

[57] ABSTRACT

A breathable non-woven fabric having barrier capabilities to biological liquids comprised of at least one non-woven layer bonded to at least one surface of a thermoplastic microporous film, the non-woven composite fabric providing a barrier to passage: (a) of biological liquid when the composite fabric is subjected to contact with synthetic blood under the dictates of testing procedure ASTM ES21-92; and (b) to viral penetration when the composite fabric is subject to contact with φX174 bacteriophage suspension at a titer of $10^3$ PFU/mL for 5 minutes with no applied pressure, 1 minute at 13.8 kPa (2.0 PSIG), and 54 minutes with no applied pressure while maintaining a moisture of vapor transmission rate of greater than about 450 grams per square meter for 24 hours at about 75° F. and about 65% relative humidity, the non-woven composite fabric which has been thermally bonded by unwinding and contacting at least one continuous thermoplastic non-woven web to at least one side of a continuous thermoplastic microporous film, continuously transporting said contacted webs and film through a thermal bonding zone and thermally bonding the webs and film at multiple spaced-apart locations, said bonding having a dwell time sufficient to thermally bond said composite while avoiding burn-through degradation of the film and webs.

24 Claims, 1 Drawing Sheet

BREATHABLE NON-WOVEN COMPOSITE VIRAL PENETRATION BARRIER FABRIC AND FABRICATION PROCESS

This application is a continuation of application Ser. No. 08/345,602, filed Nov. 28, 1994, now abandoned.

FIELD OF THE INVENTION

This invention relates to breathable non-woven composite viral penetration barrier fabrics which are impervious to water-based liquids such as body fluids but which allow passage of water vapor. Applications for such fabrics exist in the field of protective garments for medical technicians, laboratory workers, and the like where it is desired to prevent passage of blood, blood-borne pathogens or other body fluids to the body of the worker or from the worker to the patient while allowing passage of water vapor. Garments with such characteristics provide comfort for the wearer by allowing perspiration to escape, consistent with maintaining a barrier to passage blood and blood-borne pathogens.

This invention further relates to a breathable non-woven composite barrier fabric and fabrication process for the fabric wherein a non-woven web layer is thermally bonded to a microporous film of polyolefin materials either on one side only or on both sides of the microporous film. The breathable non-woven composite barrier fabric provides performance characteristics in terms of vapor transmission, body fluid and viral penetration blockage and necessary strength by selection of materials having specific physical properties for the respective layers and the microporous film which are thermally bonded into a composite fabric. Fabrics employing the invention are effective for use in protective garments where stoppage of body fluids and blood-borne pathogens is achieved, along with enhanced comfort and permeability to vapors produced by perspiration. The composite fabric may be fabricated from available materials inclusive of non-woven webs and microporous films that are readily fabricated utilizing continuous webs and microporous film which are continuously transported in contact through a thermal bonding zone achieving a composite fabric with multiple spaced-apart thermal bonds, said bonds being provided while avoiding burn-through degradation of the film and webs, thereby forming the thermally bonded non-woven composite fabric.

Microporous films have a structure that enable vapors to flow through the films while blocking liquids. The effective pore size is at least several times the mean free path of the flowing molecules, namely from several micrometers down to about 100 angstroms. Such films are generally opaque, even when made of a transparent material because the surfaces of the internal structure scatter visible light. The term "microporous film" as used herein is inclusive of microporous membranes.

Microporous films and combinations of said films with various layer materials have been utilized in a wide variety of applications. The microporous films have been used individually in applications for filtration of solids, as diffusion barriers or separators in electrochemical cells and in the preparation of synthetic leather, or cloth laminates. Use as cloth laminates require permeability of water vapor while substantially blocking liquid water for applications such as synthetic shoes, raincoats and outerwear and the like. Microporous films are also utilized for filter cleaning antibiotics, drug-time release films, beer, oils, bacteriological broths, microbiological samples, intravenous fluids, vaccines and the like. These films have also been utilized to make surgical dressings, bandages and other fluid transmissive medical applications. Such microporous films generally need to be laminated in order to fabricate garment materials for purposes of strength. The microporous films or membranes without lamination by web materials generally do not have sufficient strength to produce suitable garment materials.

Thermally bonded composites of microporous films, i.e., the combination of microporous film and web materials are frequently applied to situations requiring vapor permeability while presenting some form of barrier to the passage of water and/or aqueous solutions or aqueous suspensions, however, none of these materials have been found to be effective in combining strength of fabric, barrier limits defined by ASTM standards for passage of body fluids and body fluid-borne pathogens coupled with sufficient breathability for utilization in medical garment fabrication.

BACKGROUND OF THE INVENTION

Breathable multi-layer barrier fabrics of various combinations of layered material are disclosed in prior art patents. U.S. Pat. No. 4,041,203, issued Aug. 9, 1977, to Brock et al., discloses a fabric made up of a mat of generally discontinuous thermoplastic microfibers as a top layer and a web of substantially continuous, randomly deposited polymer filaments as a bottom layer, the layers being bonded at intermittent discrete regions. A three-layer fabric having a mat layer on the outside and a web layer in the middle is also disclosed. The specific polymer materials used for the mat and the web include polyolefins such as polypropylene. U.S. Pat. No. 4,828,556, issued May 9, 1989, to Braun et al., discloses a multi-layer fabric having a first layer of porous melt-blown material, a second layer comprised of a non-microporous film of polyvinyl alcohol, and a third layer of porous non-woven material in the form of a spun-bonded or melt-blown web. The fabric of this reference is said to be useful for absorbent articles such as diapers. Numerous prior patents directed to microporous films are also disclosed and discussed in this reference. Impervious, absorbent barrier fabrics are disclosed in U.S. Pat. No. 4,379,192, issued Apr. 5, 1983, to Wahlquist et al., the fabric including layers having continuous filament webs, microfiber mats, and polymeric film, the mats providing an uncompacted absorbent center layer.

In addition, various orientated microporous films are presented in U.S. Pat. No. 4,867,881, issued Sep. 19, 1989, to Kevin E. Kinzer, which discloses a microporous article comprising a thermoplastic polymeric structure having a plurality of cells with adjacent cells being interconnected by passageways to provide a network of communicating pores with the structure being orientated in at least one direction. Laminated structures of these same microporous materials are presented having at least one other material laminated to the microporous film are disclosed is U.S. Pat. No. 4,539,256, issued Sep. 3, 1985, to Gene H. Shipman. Porous film composites are disclosed in U.S. Pat. No. 5,169,712, issued Dec. 8, 1992, to William T. Tapp wherein porous film composites having at least one layer of an orientated polymeric porous film comprised of ethylene-propylene co-polymers and other specific polymer requirements are disclosed. While numerous combinations of layers of various polymeric materials prepared in a desired physical form are disclosed in these references in combination with microporous films, the combination of an inner layer of microporous film and outer layers of non-woven materials which are thermally bonded into a composite fabric having minimum strength, vapor permeability and body fluid barrier capabilities as disclosed herein are not known to have been disclosed or suggested by the prior art.

Other porous film composites are disclosed in the Japanese Patent Application, Kokai, No. 63-276533, publication date Nov. 14, 1988, inventors Kawano et al., entitled "Laminated Film". The Japanese reference "Laminated Film" does not provide a liquid barrier in fact presents a filtered-type product which readily flows liquid and would be suitable for example as a separator in an electrochemical cell. A breathable non-woven composite barrier fabric for protective garments should provide for wear comfort by enabling passage of water vapor resulting from perspiration or humidity in the environment, as well as forming a barrier to passage of body fluids such as blood. For effectiveness in situations involving handling of patients, the barrier should be effective at elevated pressure to prevent the blood from being projected or soaked through the fabric. In addition, strength and durability are a necessity in the fabric as exemplified by breaking strength as defined by ASTM D751 (Grab Method) and Mullen burst test values. Such protection from passage of body fluids, i.e. blood is present in U.S. patent application Ser. No. 08/087,003, filed Jul. 2, 1993, entitled "A Breathable Non-Woven Composite Barrier Fabric and Fabrication Process", hereby incorporated by reference.

SUMMARY OF THE INVENTION

The present invention discloses a breathable non-woven composite barrier fabric and a fabrication process for preparing said fabric. The fabric has unique performance characteristics of minimum levels regarding vapor permeability, barrier to passage of biological fluids, body fluid-borne pathogens and sufficient fabric strength to meet day-to-day requirements of the fabrics when utilized in protection garments. The non-woven composite fabrics are constructed of a microporous thermoplastic film having at least one film surface thermally bonded to a layer of non-woven thermoplastic materials, the film and layers being thermally bonded at multiple spaced-apart locations. These non-woven composite fabrics provide a barrier to passage of biological fluid and borne pathogens when the composite fabric is subjected to contact with synthetic blood at 0 psi for 5 minutes followed by synthetic blood contact at 2 psi for 1 minute followed by synthetic blood contact at 0 psi for 54 minutes, the composite fabric exhibiting no visible penetration of the synthetic blood. This non-woven composite fabric performance meets the requirements of ASTM designation ES 21-92 entitled "Emergency Standard Test Method for Resistance of Protective Clothing Materials to Synthetic Blood" which is hereby incorporated by reference. Further, these non-woven composite fabrics provide a barrier to penetration by body fluid-borne pathogens using viral penetration as a test system. This non-woven composite fabric performance meets the requirements of ASTM designation ES22-92 entitled "Emergency Standard Test Method for Resistance of Protective Clothing Materials to Penetration by Blood-Borne Pathogens Using Viral Penetration as a Test System" which is hereby incorporated by reference. In addition to the barrier performance of the fabric, the fabric is capable of having a moisture or vapor transmission rate of greater than about 450 grams per square meter for 24 hours at a temperature of about 75° F. and a relative humidity of about 65%. These moisture or vapor transmission rates are determined by ASTM designation E96-80 entitled "Standard Test Methods for Water Vapor Transmission of Materials" and hereby incorporated by reference. The ASTM E96-80 test utilizes two testing methodologies, Upright Cup Method and Inverted Cup Method. In addition the fabrics according to the invention in order to be utilized as protective garments for example in the medical field must have a suitable strength such as a breaking strength of at least about 14 pounds.

It has been found that thermally bonded non-woven composite fabrics do not meet these physical performance criteria readily due to burn-through of the thermal bonding thus disruption of the physical characteristics which are required. The thermal bonding of the composite fabric at multiple spaced-apart locations can be achieved by ultrasonic point bonding and one or more layers or webs can be utilized in combination with one or more microporous films. A process for forming the thermally bonded non-woven composite fabrics is also presented wherein the fabrics have these physical performance characteristics. The process includes unwinding and contacting at least one continuous thermoplastic non-woven web to at least one side of a continuous thermoplastic microporous film, continuously transporting said contacted webs and film through a thermal bonding zone. The thermally bonding of the webs and film are at multiple spaced-apart locations. The thermal bonding is achieved under control dwell time which allows appropriate bonding for strength basis and yet avoids burn-through degradation of the composite webs and film.

It is, therefore, an object of this invention to provide a breathable non-woven composite barrier fabric comprised of thermoplastic materials which are fabricated through thermal bonding and have capabilities for providing permeation of water vapor while simultaneously providing a barrier against passage of water-based fluids such as body fluids and body fluid-borne pathogens.

Another object of the invention is to provide such a fabric that provides a barrier to the passage of blood under the dictates of ASTM designation ES21-92, the current designation for use in medical and related protective garments.

Yet another object is to provide a breathable non-woven composite barrier fabric that can be fabricated using multiple spaced-apart thermal bonding on readily available thermoplastic materials.

In still another object is to provide such a fabric that provides a barrier to viral penetration under the dictates of ASTM designation ES22-92, the current designation for use in medical protection garments.

Other objects and advantages of the invention will be apparent from the following detailed description and the appended claims.

DESCRIPTION OF THE PREFERRED EMBODIMENT

Figure 1:
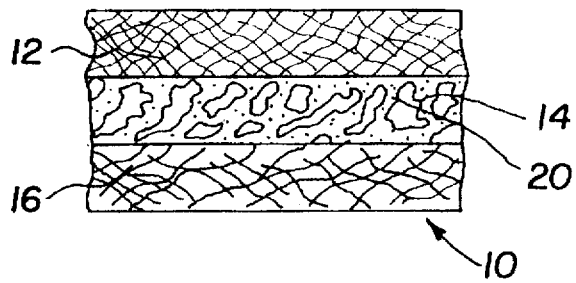
FIG. 1 is a diagrammatic representation of a cross-sectional view of a multi-layer composite fabric embodying the invention.

Referring to the drawings, there is shown a breathable non-woven composite barrier fabric 10 made up of three layers, a top layer 12 of a spun-bonded polyolefin, a middle layer 14 of a microporous thermoplastic film, and a bottom layer 16 of spun-bonded polyolefin. The three layers are secured to one another by thermal or ultrasonic bonding at spaced-apart points 18 throughout the fabric surface.

Top layer 12 may be comprised of a non-woven polyolefin with the microporous thermoplastic film middle layer 14 preferably being comprised of polypropylene or any other thermoplastic materials which will accept point thermal bonding or ultrasonic bonding and maintain the minimum performance levels as defined. As performance levels are achieved by strengthening the composite fabric by thermal point bonding as well as avoiding burn-through of the microporous film and webs and also avoiding melt flow closure of the porosity of the microporous film.

The non-woven thermoplastic layer of web materials have a weight of from about 0.2 to about 2.5 ounces per square yard with about 0.5 to about 1.0 being preferred. The non-woven layers are preferably spun-bonded providing strength to the composite fabric along with a cloth-like surface texture which enhances the use of the fabric for garments, as contrasted to film materials which have a smooth plastic surface. Spun-bonded polypropylene or polyethylene or co-polymers of polyolefins are suitable for use in the fabrication of the breathable non-woven composite barrier fabric and are available from various sources. Spun-bonded polyolefin suitable for this purpose is available from Poly-Bond, Inc. under the designation "Poly-Bond". Properties of such spun-bonded webs useful in accordance with the fabrication of the present fabric are achieved with a wide range of web weights, however suitable thermally bonded composites result from the lower weight webs as well as the higher weight webs. The nonwoven webs have a grab strength in machine direction of at least 6.5 pounds to break, cross-directional of at least 5 pounds to break and an elongation value of at least 52% machine direction and at least 72% cross-direction.

The bottom layer 16 may have the same composition as top layer 12, although top layer 12 and bottom layer 16 may be comprised of different materials and have different web weights and be suitable for utilization in the thermally bonded non-woven composite barrier fabric. The middle layer 14 is comprised of a microporous film of a thermoplastic material which maintains its porosity without burn-through when thermally bonded in fabrication of the composite with the thermoplastic webs or layers. Preferably the microporous film is comprised of polypropylene which is amenable to point thermal bonding, specifically ultrasonic point thermal bonding at bonding point 18, without experiencing burn-through in controlled conditions. The polypropylene films have a microporous structure with extremely small random pores 20 extending through the film matrix, allowing vapor such as water vapor to pass through, while forming a barrier to passage of liquids such as body fluids. A suitable microporous film material is available from several commercial sources and can be formed by the steps of:

(a) forming a homogeneous blend of propylene-based resin and about 0.5 to about 10 ppm of a nucleating agent capable of producing beta-spherulites, (b) extruding the blend into a film having a thickness of about 0.01 to about 0.4 millimeters on a cast film line having a chill roll temperature of about 90° to about 130° C., (c) cooling the film below the crystallization temperature of the propylene-based resin to form at least 20 wt. % beta-spherulites in the film, (d) extracting beta-spherulites corresponding to at least 15 wt. % of the blend from the cast film by immersing the cast film in a toluene bath at a temperature of about 85° to about 95° C. for a time period of 10 minutes or less to form a porous film and drying the porous film at a temperature of about 15° to about 110° C. for 20 minutes or less, and (e) orienting the porous film by heating the porous film at a temperature of about 115° to about 135° C. for a time period of about 2 to about 20 seconds and stretching the heated porous film in at least one direction at a stretch ratio of about 1.5 to about 7.5 to form the oriented porous film.

The oriented porous film described above can have a MVTR of about 2,000 g/m$^2$/24 hr or greater as determined according to ASTM E-96, procedure E and the propylene-based resin used to make the oriented porous film can be a polypropylene having a melt flow rate of about 1.0 to about 10 as measured by ASTM D-1238. The propylene-based resin can also be a blend of from about 70 to 100 wt. % of a polypropylene having a melt flow rate of about 1.0 to about 10 as measured by ASTM D-1238 and about 30 to 0 wt. % of an ethylene-propylene copolymer having an ethylene content of about 10 to about 50 wt. % and a melt flow rate of about 0.5 to about 10 as measured by ASTM D-1238. Optionally, a third polymeric component such as a low molecular weight polypropylene homopolymer or random copolymer can also be incorporated into the blend.

In preparing the polymeric film compositions, the composition components can be added to conventional blenders such as roll mills, drum tumblers, double-cone blenders, ribbon blenders, and the like, or any two or more of the components can be preblended or formed into a masterbatch and mixed with the remaining components in conventional blenders. The beta-spherulite nucleating agent generally in the form of powder can be dispersed in mixtures of polymeric components by any of the procedures normally used in the polymer art to ensure uniform mixing of powder and polymer resin. For example, the Q-dye in powder form can be blended with the polymer components in powder or pellet form or the Q-dye can be slurried in an inert medium and the slurry used to coat the polymer powder or pellets. Alternatively, mixing at elevated temperatures can be accomplished by using, for example, a roll mill or multiple passes through a melt-compounding extruder. A preferred mixing procedure is the blending of the nucleating agent in powder form with polymer pellets or powder followed by melt-compounding the resulting mixture in single-screw or multiple-screw extruder. Multiple passes may be necessary to ensure the desired level of dispersion of nucleating agent in the polymer. This procedure can also be used to form a masterbatch of nucleating agent and polymer. It is important that a homogeneous composition be formed so that the films prepared from the polymeric composition have a uniform distribution of the polymer components and beta-spherulite nucleating agent in order that oriented polymeric microporous films with uniform strength and breathability are obtained.

For polymeric compositions which are capable of being converted into oriented polymeric microporous films by a process including the extractive removal of beta-spherulites to form a porous film with a subsequent orientation step, the polymeric composition comprises about 5 to about 30 parts by weight of the ethylene-propylene block copolymer, about 70 to about 95 parts by weight of the polypropylene homopolymer or random copolymer of propylene and about 0.1 to about 10 ppm of the beta-spherulite nucleating agent. Porous films prepared by this process from compositions containing less than 5 parts by weight of the ethylene-propylene block copolymer do not exhibit the improved aesthetic qualities such as softer hand and decreased noise generation when flexed, whereas films prepared from compositions containing more than 30 parts by weight of the ethylene-propylene block copolymer do not exhibit sufficient porosity. Oriented porous films prepared from compositions comprising about 5 to about 30 parts by weight of the ethylenepropylene block copolymer by a process including the formation of a porous film by the extractive removal of beta-spherulites have improved aesthetic qualities such as a softer hand and decreased noise generation when flexed and good breathability properties as measure by MVTR.

The amount of beta-spherulite nucleant useful in forming porous films by the extractive removal of beta-spherulite technique from the polymeric compositions of this invention depends on the effectiveness of the particular nucleant for inducing beta-crystals and the amount of porosity desired in the porous film. For the Q-dye, the amount present in the polymeric compositions can range from about 0.01 to about 50 ppm by weight. Sufficient nucleating agent is employed to induce the formation of 20 wt. % or more of beta-spherulites in the film. Preferably, about 0.1 to about 10 ppm by weight of Q-dye is utilized. Other things being equal, less than about 0.01 ppm of Q-dye has a negligible effect on the level of beta-form spherulites present in the film, and amounts greater than 50 ppm do not significantly increase the amount of beta-spherulites formed. For compositions with about 0.1 to about 10 ppm of Q-dye acting as a nucleating agent and formed into a film, a sufficient amount of beta-spherulites is formed in the film such that a high porosity film is formed when the film is extracted with toluene, carbon tetrachloride or xylene. With a subsequent orientation step, a film having increased porosity and breathability is formed.

For compositions including a beta-spherulite nucleating agent, a critical parameter in the formation of beta-spherulites in the film is the rate at which the film is cooled. Other parameters being equivalent, the more rapid the cooling, the smaller the size of the beta-spherulites formed. If the molten film is cooled too rapidly, it is possible that essentially no beta-spherulites are formed. Conversely, the slower the film is cooled, the larger the size of the beta-spherulites formed. Little or no beta-spherulites are formed below about 80° C. or above about 130° C. The cooling conditions needed to achieve the desired beta-spherulite size can be controlled by one or more of the following parameters: polymer melt temperature, extrusion rate, drawdown ratio, die gap and chill roll temperature for extruded film, and cooling air velocity and temperature for blown film. Other things being equal, an increase in one of the following parameters results in a decrease in the rate at which the molten film is cooled or quenched and, consequently, an increase in the size of the beta-spherulites formed: polymer melt temperature, extrusion rate, die gap, cooling air temperature, and chili roll temperature. Conversely, other things being equal, a decrease in one of these variables results in a decrease in the size of the beta-spherulites. By contrast, other things being equal, an increase in either the drawdown ratio or cooling air velocity results in an increase in the quench rate and an associated decrease in the size of the beta-spherulites formed.

For polymeric compositions capable of being formed into microporous films by a process including the extraction of beta-spherulites from formed films, the film is ordinarily at least about 0.005 millimeters in thickness. The useful maximum thickness depends on the time of extraction of the beta-spherulites. Other things being equal, the thicker the film, the longer the time required to extract a given percentage of the total beta-spherulites present. The beta-spherulites formed in the film can be extracted with nonpolar, organic solvents. For ease of operation, it is preferred that the extracting medium having a boiling point greater than about 100° C. It is possible to utilize mixtures of two or more organic solvents and in such an event the lower boiling solvent should have a boiling point greater than about 100°

C. Preferred extraction solvents include toluene, carbon tetrachloride, and xylene, with toluene being more preferred. Any conventional extractive technique used in the extraction of films can be used. Particularly useful are processes which include temperature- and environment-controlled extraction vessels which permit complete immersion of the films in the extraction solvent at a controlled temperature and under conditions in which any extraction solvent vapors are contained.

The extraction conditions are critical in selectively removing at least a portion of the beta-spherulites while minimizing the amount of alpha-form crystalline polypropylene removed. Removal of the beta-form crystals is very temperature dependent. If the extraction temperature is too low, the beta-spherulites are removed too slowly or not at all; and, if the extraction temperature is too high, alpha-form crystals are dissolved along with the beta-form. The optimum temperature of extraction depends on the particular extraction medium used and can be readily determined by one skilled in the art. For the preferred extracting medium, toluene, the extraction is preferably accomplished in the temperature range of about 85° to about 95° C., most preferably about 88° to about 93° C. It has also been found that for films containing cornstarch extraction temperatures which are about 3° to 5° C., lower can be used.

The extraction time, used herein to mean the time the film contacts the extracting medium at the extraction temperature, relates to the extraction temperature. Other things being equal, the higher the extraction temperature, the shorter the extraction time; conversely, the lower the extraction temperature the longer the film must be in contact with the extraction medium to remove a given amount of beta-spherulites. The length of the extraction time can be used to control the degree of porosity to some extent since at a given extraction temperature greater quantities of the beta-spherulites can remain in the film as the extraction time is decreased. It is preferred that up to 15 wt. % of the beta-spherulites be extracted as measured by weight loss in the extruded film. The extraction time also depends on the thickness of the film being extracted. At a given temperature, the extraction time increases as the film become thicker. Ordinarily the extraction time ranges from about 1.5 to about 20 minutes. Preferably, the extraction time is 10 minutes or less.

The extracted film can be dried at a drying station to remove any extraction solvent which remains with the film. The drying station can be any conventional means used to remove materials such as extraction solvents. Devices such as radiant heaters can be employed with the preferred drying method utilizing a blower for impinging heated air on the film. With both the drying station and the extraction vessel, environmental procedures involved in handling extraction solvents and their vapors are utilized. It is preferred that extraction vessels and the drying stations be contained in a housing equipped with exhaust and volatiles treatment facilities to minimize loss of the extraction solvent to the environment.

In the orienting step, the extracted, porous film can be stretched uniaxially or biaxially at stretch ratios of about 1.5 to about 7.5. Uniaxial stretching methods include rolls, and a roll or tenter for restraining the film. Biaxial stretching methods include successive uniaxially stretching comprising longitudinal stretching by rolls and transverse stretching by a tenter and simultaneous biaxial stretching using a tenter. For biaxial stretching, the stretch ratio in the longitudinal or machine direction and transverse direction may be the same or different. Preferably the thickness of oriented films produced from the polymeric compositions of this invention ranges from about 0.005 millimeters to about 0.2 millimeters in thickness. The unstretched porous films from which the oriented films are formed range in thickness from about 0.01 to about 0.4 millimeters.

In a particular embodiment the porous film composite of this invention comprises at least one layer of an oriented polymeric porous film having polygonal cells with average greatest dimensions of about 5 to about 30 microns and interconnecting pores between the cells having average diameters of about 0.2 to about 20 microns.

Properties of a designated film suitable for use in this invention are as follows: thickness, 1.5 mil; weight, 0.85 ounce per square yard; tensile strength at break (DPD Test Method 106), machine direction, 2,000 g/25 mm; cross direction, 950 grams/25 mm; elongation at break (DPD Test Method 106), machine direction, greater than 100 percent, cross direction, greater than 100 percent. Permeation/barrier properties include a moisture vapor transmission rate of greater than about 2,000 grams per square meter per 24 hours at 75° F. and 50% relative humidity as measured by the inverted cup method; air permeability, less than 400 seconds/50 cc by Gurley Densometer® measurement and water hold-out, greater than 45 pounds per square inch as measured by Mullen burst test. Other microporous films having a moisture vapor transmission rate of greater than 1,500 g/m²/24 hr. at 86° F. and 48 percent relative humidity as measured by ASTM E96 and water holdout greater than 50 psi are acceptable.

Thermoplastic polymers useful in the present invention include olefinic, condensation and oxidation polymers. Representative olefinic polymers include high and low basis weight polyethylene, polypropylene, polyvinyl containing polymers, butadiene containing polymers and the like. Condensation polymers include polyesters such as polyethylene terephthalate and polybutylene terephthalate, polyamides such as nylon 6, nylon 13 and nylon 66, polycarbonates and polysulfones. Polyphenylene oxide is representative of the oxidation polymers which can be used. Blends of thermoplastic polymers may also be used. However, while most of these thermoplastic polymers can be utilized in forming a suitable web for combining with microporous film, the microporous film must be comprised of polymeric materials, i.e. thermoplastics, which can survive thermal bonding, ultrasonic point bonding and the like without degenerating due to burn-through thus losing the barrier properties and yet maintaining moisture vapor permeability, i.e. through point bonding versus hot roll thermal bonding.

As used herein, the term "thermoplastic polymer" refers only to conventional polymers, both crystalline and noncrystalline, which are melt processible under ordinary melt processing conditions and does not include polymers such as polytetrafluoroethylene which under extreme conditions, may be thermoplastic and melt processible. One suitable microporous film utilized in accordance with the present invention may be provided by the processes as defined in U.S. Pat. No. 5,208,098, issued May 4, 1993, entitled "Self-Bonded Nonwoven Web and Porous Film Composites" which is hereby incorporated by reference.

Major limitations of prior porous film composites comprising layers, of microporous film and a second material include the ability to form a porous film composite which retains the vapor permeability of the porous film while at the same time not contributing greatly to the stiffness or bulk of the composite from the addition of the other material and avoidance of burn-through conditions and thermal bonding or blockage of the porosity of the porous film component either through adhesive or hot roll thermal bonding.

For example, porous film composites wherein webs are used to impart strength, especially in the cross-machine direction, the spun-bonded webs are typically non-uniform in basis weight and coverage such that the relatively thicker and thinner areas are easily recognized by the human eye. Attempts have been made to compensate for these poor fabric properties and limiting physical properties resulting from the non-conformity of basis weight and coverage by using spun bond webs having a heavier base weight than what would normally be required by the particular application. This problem also leads to burn-through of point thermal bonding materials, fabrication of composites with greater stiffness, increase bulk and other undesired features.

Thermal bonding technologies, in particular ultrasonic bondings are established tools in the industry utilizing thermoplastic materials. Use of ultrasonic energy in fabric and fiber bonding is well known and is best known in the textile industry for ultrasonically formed mattress pads and bed sheets via the pinsonic or pin point ultrasonic processing. The point bonding ultrasonic process has provided the foundation for using ultrasonic energy to laminate and/or form non-woven fabrics and products. The process has been successful because of the inherent advantages that generally apply to all welding of thermoplastic by ultrasound, including speed, efficiency, good bond integrity and elimination major melt zones.

Ultrasonic bonding presents only three process variables which are amplitude, pressure and time. Since the desired result is ultimately energy to melt and bond fibers, it can be simply stated that power is a function of ultrasonic horn vibration amplitude and pressure and that energy is a function of power used and time. These process variables are roughly established by prior experience and can be adjusted to meet the needs of the specific application which has desired melt depth, thickness of traveling webs and composites and adjustability of the ultrasonic horns in relationship to the traveling webs which are being thermally, i.e. ultrasonic point bonded. The dimensional relationship with a pattern roll which is in a fixed position having multiple pins mounted thereon defines in cooperation with the horn surfaces a gap for travel of the contacted webs and microporous films. Other variables that become fixed are web area, fiber type and amount of fiber. Within certain limits, the ultrasonic variables can be changed in relationship to one another in order to acquire a constant result. However, changes in non-ultrasonic variables such as fiber type, blend or weight will require one or more new changes in the ultrasonic variabilities to ensure adequate energy to the bonded area.

A major difference in ultrasonic bonding and thermal bonding is that heat energy is not conducted through the fiber to be bonded but instead generated within the fiber itself, minimizing degradation of material through excessive heat. In addition, ultrasonic processing is faster with reported speeds in excess of 100 feet per minute. In general, the pattern roll with multiple pin extensions for grading pressure proximity of the ultrasonic horn surfaces are air cooled in order to avoid undue thermal buildup which would be detrimental to, for example, the microporous characteristics of the microporous film.

The ultrasonic bonding process in accordance to the invention for fabricating breathable non-woven composite barrier fabric utilizes a pattern roll which is in an affixed position having pins extending therefrom with approximate diameters of about 0.5 min. However the ultrasonic bonding apparatus can be improved by modifying dwell time through use of elongated pins of about the same cross-section, i.e. 0.5 min. As the contacted webs and microporous film travel rate through the ultrasonic processing zone at 26 yards per minute, a contact time of the pin with the contacted webs and film is determined to be about 1.3 milli-seconds. Reduction of speed of travel of the contacted webs and microporous film will provide stronger bonding for lighter non-woven areas or lighter non-woven webs. In any case, the dwell time of the traveling contacted webs and microporous film through the ultrasonic bonding zone must be carefully controlled in order to avoid burn-through degeneration of the film and webs and the apparatus must have adjustability of the gap in order to accommodate the various thicknesses of materials presented in the contacted webs and films.

The breathable non-woven composite barrier fabric according to the invention can be utilized in cooperation with various additives such for example as antistatic compounds. Since many antistatic compound additives perform as wetting agents, generally the antistatic compounds are added to the web surface which will be next to the user, thus avoiding any wetting of the environmental surface which will be exposed to body fluids and the like. By adding the antistatic materials to the user side of the fabric, the performance criteria of the fabric is not compromised; however, selected known antistatic compounds having lesser wetting characteristics can be added to both sides of the fabric as long as the minimum fabric performance criteria is maintained. In addition the fabrics according to the invention can be sterilized for use in sterile environment requirements such as medical and certain laboratory and manufacturing operations. Depending on the thermoplastic polymers comprising the fabric, this sterilization can be achieved through, for example, radiation and chemical sterilization such as through the use of ethylene oxide. Ethylene oxide is preferable when utilizing polypropylene thermoplastic polymers, however, other suitable sterilization compounds and techniques can be utilized if such sterilization procedures do not compromise the minimum performance levels of the fabric.

The invention is further illustrated by the following examples, comparative examples and test procedure methods.

Emergency Standard Test Method for Resistance of Protective Clothing Materials to Synthetic Blood (ASTM ES21-92)

Workers, primarily those in the health care profession, involved in treating and caring for individuals injured or sick, can be exposed to biological liquids, capable of transmitting disease. The diseases, which may be caused by a variety of microorganisms, can pose significant risks to life and health. This is especially true of bloodborne Hepatitis B, Hepatitis C, and Human Immunodeficiency Viruses, which are related to Hepatitis and AIDS. Since engineering controls cannot eliminate all possible exposures, attention is placed on reducing the potential or direct skin contact through the use of protective clothing that resists penetration. Chemical molecular diffusion is not recognized as a transmission mode for microorganisms. This test method determines resistance to penetration of blood and other body fluids using synthetic blood.

Scope

This test method covers the determination of the resistance of protective clothing materials to penetration by biological liquids using synthetic blood under the condition of continuous liquid contact. Protective clothing material "pass/fail" determinations are based on visual detection of synthetic blood penetration.

This test method has been designed to measure the effectiveness of protective clothing barrier material properties using a synthetic blood mixture. It may be used as a preliminary screen for penetration of blood and other body fluids.

The synthetic blood mixture is prepared with a red dye to aid in visual detection and with a surfactant to simulate the surface tension of blood.

This test method may not apply to all forms or conditions of biological liquid exposure. Users of the test method should review tasks for worker/clothing exposure and assess the appropriateness of this test method for their specific applications.

The values in SI units shall be regarded separately as standard. The values stated in each system must be used independently of the other, without combining values in any way.

This standard does not purport to address all of the safety problems, if any, associated with its use. It is the responsibility of the user of this standard to establish appropriate safety and health practices and determine the applicability of regulatory limitations prior to use.

Summary of Test Method

This resistance of a protective clothing material to penetration by a biological liquid (synthetic blood) is determined using a modified form of Test Method F 903. The same test apparatus and specimen exposure format are used. Exposure Procedure C from Test Method F 903 is used for the test. This procedure subjects the material to synthetic blood at 0 psi for 5 minutes followed by 2 psi (13.6 kPa) for 1 minute followed by 0 psi for 54 minutes and noting whether visible penetration occurs.

In the test apparatus, the clothing material acts as a partition separating synthetic blood from the viewing side of the test cell.

A minimum of three specimens are tested. Results are reported as "pass/fail". Any evidence of synthetic blood penetration constitutes failure.

Significance and Use

This test method is based on Test Method F 903 for measuring resistance of chemical protective clothing materials to penetration by liquids. It is normally used to evaluate specimens from finished items of protective clothing.

Finished items of protective clothing include gloves, arm shields, apron, gowns, suits, hats, boots, and the like.

The phrase "specimens from finished items" encompasses seamed and other discontinuous regions as well as the usual continuous/regions of protective clothing items.

This test method can be used to identify protective clothing materials and constructions that limit exposures to biological liquids.

Protective clothing materials are intended to be barriers to blood and other body fluids that may contain infectious agent. The use of synthetic blood may not reflect the properties of all body fluids which can contain infectious agents. Therefore, in order to simulate the wetting characteristics of blood and body liquids, the surface tension of the synthetic blood is adjusted to approximate the lower end of the surface tension range.

This test method involves a qualitative determination of the protective clothing material resistance to penetration by synthetic blood under specific test conditions. It may be suitable for use as a material quality control or assurance procedure.

Part of the protocol for exposing the protective clothing material specimens with synthetic blood involves pressurization of the test cell to 13.8 kPa (2 psig). This pressure has been documented to discriminate between protective clothing material performance and correlate with visual penetration results that are obtained with a human factors validation.

Test Specimen

Each material specimen to be tested shall have a minimum dimension of 64 mm (2.5 in.). A 70 mm (2.8 in.) square is convenient.

A more simplified test showing approximately the same barrier test result are shown in the following elbow test procedure. Results of the ASTM blood barrier test and the elbow test are correlatable in general.

ELBOW TEST

Instructions for Using the Synthetic Blood Barrier Demonstration Kit

CAUTION: Synthetic blood will permanently stain clothing and skin. Use special care during the use of this kit.
1. Remove the ink pad from plastic bag.
2. Remove top from synthetic blood bottle and liberally apply the blood to the pad by gently squeezing the bottle.
3. Remove blotter paper and material samples from their respective plastic bags.
4. Place breathable non-woven composite barrier fabric swatch over the ink pad with the material's normal outside surface against the pad.
5. Place blotter paper, shiny (coated) side up, on top of material sample.
6. Firmly apply pressure to the blotter paper with elbow.
7. Remove the blotter paper and turn bottom side up for visual examination.
8. Stains on the blotter paper indicate blood strikethrough.

The non-woven composite fabric according to the invention must also provide in addition to the barrier performance, a water vapor transmission rate which is designated under ASTM E96-80, excerpts which are provided herein below. Standard Test Method for WATER VAPOR TRANSMISSION OF MATERIALS Designation: E96-80

Scope

These methods cover the determination of water vapor transmission (WVT) of materials through which the passage of water vapor may be of importance, such as paper, plastic films, other sheet materials, fiberboards, gypsum and piaster products, wood products, and plastics. The methods are limited to specimens not over 1¼ in. (32 mm) in thickness except as provided in Section 9. The two basic methods, Upright Cup and Inverted Cup Water Method, are provided for the measurement of permeance, and two variations include service conditions with one side wetted and service conditions with low humidity on one side and high humidity on the other. Agreement should not be expected between results obtained by different methods. That method should be selected which more nearly approaches the conditions of use.

Summary of Methods

In the Upright Cup Method the test specimen is sealed to the open mouth of a test dish containing distilled water and the assembly placed in a controlled atmosphere. Periodic weighings determine the rate of water vapor movement through the specimen.

In the Inverted Cup Water Method (water resting on specimen), the dish contains distilled water, and the weighings determine the rate of vapor movement through the specimen from the water to the controlled atmosphere.

Significance and Use

The purpose of these tests is to obtain, by means of simple apparatus, reliable values of water vapor transfer through permeable and semipermeable materials, expressed in suitable units. These values are for use in design, manufacture, and marketing. A permeance value obtained under one set of test conditions may not indicate the value under a different set of conditions. For this reason, the test conditions should be selected that most closely approach the conditions of use.

Moisture vapor transmission rates for fabrics or continuous materials are determined on a basis of grams per meter square per 24 hours. The one procedure since several procedures are used in the industry, the material to be tested is fastened over the mouth of a dish which contains water. The assembly is placed in an atmosphere of constant temperature of about 90° F. and a relative humidity of 50% plus or minus 5% and the weight loss of the assembly is used to calculate the rate of the moisture vapor permeability through the test material. The moisture vapor transmission rate (MVTR) is calculated as follows:

$$\text{Moisture of Vapor Transmission Rate (MVTR)} = w \times 24/(t \times a)$$

Where:
w=weight loss (grams)
t=test time (hours)
a=exposed area of specimen (meters square)

The preceeding MVTR procedure was utilized in providing the performance date of Table 1 below wherein non-woven composite fabric materials according to the invention were taken.

| 0.9 polypropylene web/polypropylene film/0.5 polypropylene web | |
|---|---|
| Test Conditions: | Water Method at 23 C. |
| Average Thickness: | 17.5 mils |
| Test Temperature: | 26 C. |
| Relative Humidity: | 54% |

TABLE 1

| Trial Number | Time of Exposure (hours) | WVT (g/m2-24 hour) | Minimum Detectable |
|---|---|---|---|
| 1 | 8 | 530 | 5 |
| 2 | 8 | 571 | 5 |
| 3 | 8 | 456 | 5 |
| | Average: 519 | | |
| | Standard Deviation: 47.6 | | |

WVT = Rate of water vapor transmission, given in grams per square meter per 24 hours Emergency Standard Test Method for Resistance of Protective Clothing Materials to Penetration by Blood-Borne Pathogens Using Viral Penetration as a Test System

ASTM ES22-92

Scope 1.1 This test method is used to measure the resistance of protective clothing materials to penetration to blood-borne pathogens by using a surrogate microbe under the condition of continuous liquid contact. Protective clothing "pass/fail" determinations are based on detection of viral penetration.

1.1.1 This test method may not be effective in testing protective clothing materials having thick, inner liners which readily absorb the liquid assay fluid.

1.2 The test method has been designed to measure the effectiveness of protective clothing material against bloodborne pathogens using a microbiological model.

1.2.1 The chosen simulant, bacteriophage Phi-X174 was selected as the most appropriate model for blood-borne pathogens because of its small size, spherical morphology, environmental stability, non-human infectivity, high assay sensitivity, rapid assay and high titer.

1.2.2 Bacteriophage Phi-X174 best approximates Hepatitis C virus in size but also may be used as a surrogate for Hepatitis B virus and the Human Immunodeficiency Virus (HIV).

1.3 This test method may not apply to all forms or conditions of blood-borne pathogen exposure. Users of the test method should review modes for worker/clothing exposure and assess the appropriateness of this test method for their specific applications.

1.4 The values state in S1 units or in other units shall be regarded separately as standard. The values stated in each system must be used independently of the other, without combining values in any way.

1.5 This standard does not purport to address all of the safety problems, if any, associated with its use. It is the responsibility of the user of this standard to establish appropriate safety and health practices and determine the applicability of regulatory limitations prior to use.

The following describes details and results for the microbiological viral penetration testing of protective clothing materials, which are to be used to protect against bloodborne pathogen hazards. The test procedure was adapted from the ASTM ES 22 procedure developed by the ASTM Subcommittee F23.40 on Biological Hazards. The test device used in this procedure was the ASTM F903 Chemical Penetration Cell.

The bloodborne pathogens of major concern are the hepatitis B virus (HBV), hepatitis C virus (HCV) and human immunodeficiency virus (HIV). HBV is enveloped, spherical, and 42–47 nm (nonometers) in size. HCV has no envelope, icosahedral morphology, and is 27–30 nm in size. The blood serum concentrations of these three bloodborne pathogens ranges from less than 100 to more than 100 million IU/mL (infectious units per milliliter). The φX174 bacteriophage is one of the smallest known viruses. It has no envelope, has icosahedral morphology, and is 25–27 nm in size. The φX174 bacteriophage challenge suspension will be maintained at a concentration of at least $1.0 \times 10^8$ PFU/mL (plaque forming units/mL).

Test specimens were challenged with approximately 60 mL of a φX174 bacteriophage suspension for 5 minutes at atmospheric pressure, 1 minute at 2.0 PSIG (13.8 kPa), and 54 minutes at atmospheric pressure or until liquid penetration was observed. At the conclusion of the test, the observed side of the test specimen was rinsed with a sterile assay medium and then assayed for the presence of the φX174 bacteriophage. The surface tension of the challenge suspension and the assay medium was adjusted to approximately 40–44 dynes/era using surfactant-type Tween® 80 at a final concentration of approximately 0.01% by volume.

JUSTIFICATION

The protective clothing materials tested are intended to provide protection against blood, body fluids, and other potentially infectious materials. The surface tension range for blood and body fluids is approximately 42–60 dynes/cm. Therefore, in order to simulate the wetting characteristics of blood and body fluids the surface tension of the φX174 bacteriophage suspension was adjusted to approximate the lower end of this surface tension range (40–44 dynes/cm).

The choice of a microbiological model to evaluate the effectiveness of the bloodborne pathogen barrier properties of protective clothing materials is important. There are problems associated with utilizing the actual bloodborne pathogens as test organisms. HBV and HCV cannot be grown in the laboratory. HIV represents a significant safety and liability consideration due to its high infectivity potential and requirements for extreme and expensive precautions.

Therefore, a model for the bloodborne pathogens was researched. The ideal properties of a surrogate would include small size, spherical or polyhedral (round) morphology, environmental stability, low or non-human infectivity, high assay sensitivity, rapid growth, and high titer. The φX174 bacteriophage was selected as the most appropriate surrogate for the bloodborne pathogens mentioned because it satisfies all of these criteria. The φX174 bacteriophage has no envelope and is 25–27 nm in sizer (similar to HCV the smallest pathogen), has an icosahedral or nearly spherical morphology similar to all three viral pathogens mentioned, has excellent environmental stability, is non-infectious to humans, has a limit of detection which approaches a single virus particle, grows very rapidly (assay results can be read within as little as 4–8 hours), and can be cultivated to reach very high titers similar to HBC (the most concentrated pathogen mentioned).

Animal virus surrogates are not used as they require specialized cell culture and enzyme assay techniques. In addition, the stability of most of the animal viruses is less than desirable and plating efficiency is low or unknown.

Despite the variety of viral coats or surfaces (i.e., lipophilic, hydrophilic, etc.), they generally perform similarly in barrier or penetration tests. This is because viruses adopt the charge of the liquid in which they are suspended and are more affected by the liquid vehicle than by their own physical or chemical properties.

It is also important to note that blood as the test vehicle, while it may seem appropriate, is actually a poor choice. Many viruses adsorb to blood cells. Red blood cells are about 7–10 μm in diameter and can actually plug pores. Since many other body fluids can be infectious, it is more severe to use a body fluid simulant (surfactant containing, particulate-free suspending liquid) such as that described in this procedure.

TEST SPECIMEN PREPARATION

The test material was randomly cut into approximately 75 mm×75 mm specimens. The thickness of each specimen was determined using a thickness dial gauge. Test specimens were gas sterilized with Ethylene Oxide (12/88) and degassed according to the following parameters:

Preconditioning: 30 minutes minimum.
Temperature: 52° C.±2° C.
Relative Humidity: 55±10%.
Gas Pressure: 15 PSIG
Exposure Time: 8 hours minimum.
Degassing Time: 48 hours minimum @ 54° C.±2° C.

Prior to testing, all test specimens were conditioned for a minimum of 24 hours at 21° C.±5° C. and 30% to 80% Relative Humidity.

CHALLENGE PREPARATION

The φX174 bacteriophage stock culture was prepared by inoculating a 100 mL aliquot of nutrient broth with *E. coli* C and incubating at 37° C.±2° C. with shaking for 14–18 hours. A 1:100 dilution of the overnight culture was prepared and incubated for approximately 90 minutes at 37° C.±2° C. The 90 minute culture was inoculated with a 0.5 mL aliquot of the φX174 bacteriophage stock (ATCC# 13706-B1) and incubated with rapid shaking for 1 to 5 hours at 37° C.±2° C. Complete lysis of the host bacteria was noted when the broth cleared. The virus suspension was centrifuged at 5000×G for 20 minutes and the supernatant was filtered through a sterile 0.45 µm filter and then through a 0.22 µm filter to remove the host cell debris. The φX174 stock culture was kept refrigerated at 2°–8° C. The titer of the stock culture was periodically determined to verify concentration.

The φX174 challenge suspension was prepared by diluting the φX174 stock culture in sterile nutrient broth with 0.01% Tween® 80 to provide a challenge concentration of $\geq 1 \times 10^8$ PFU/mL and a final surface tension of 40–44 dynes/cm.

TEST PROCEDURE

Figure 2:
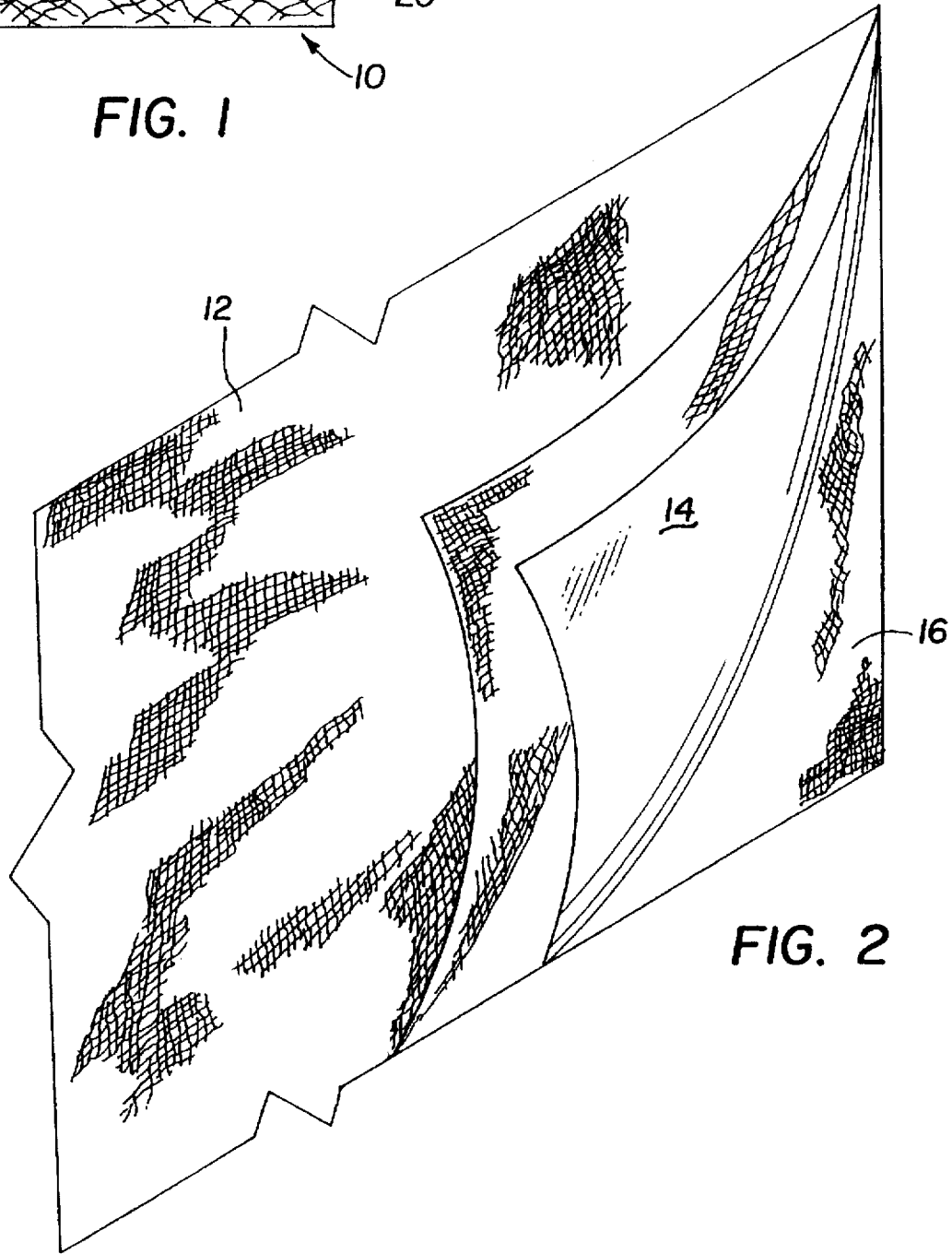
FIG. 2 is a schematic fragmentary perspective view, with portions peeled away, of the fabric of FIG. 1.

Prior to testing, the penetration test cells were steam sterilized at 121° C. for 30 minutes minimum. This included the cell support, Teflon® cell, gaskets, retaining screen (optional), drain valve, airline connector, stainless steel flange, and nuts. After the test cells cooled to room temperature, the sterile test specimen was placed into the penetration cell with the normal outside surface of the specimen oriented toward the test cell reservoir, using exposure option A from Appendix 1. The inner side surface of the specimen was observed for liquid penetration. The layers were clamped into the test cell in the following order (see FIG. 2):

Teflon® cell.
Gasket.
Test sample.
Gasket.
Retaining screen (optional).
Gasket.
Stainless steel flange.

Each of the bolts were torqued to 120 inch pounds, using a criss-cross technique. The penetration test cell was placed into the test apparatus and the drain valve closed (see FIG. 1). The test cell reservoir was filled with approximately 60 mL of the φX174 challenge suspension. The exposed surface of the test specimen was observed for liquid penetration for 5 minutes at atmospheric pressure. If liquid penetration was observed the test was terminated and the test specimen was assayed for φX174 penetration.

The air line was connected to the test cell at the top port. The air regulator was opened slowly to 2.0 PSIG (13.8 kPa) and the surface of the specimen was observed for liquid penetration. If liquid penetration was observed, the test was terminated immediately and test specimen was assayed for φX174 penetration. The pressure was held constant (2.0 PSIG) for exactly 1 minute and the surface of the test specimen was monitored for the appearance of liquid penetration. If liquid penetration was observed, the test was terminated immediately and the surface of the test specimen was assayed for φX174 penetration. The pressure regulator was turned to release the pressure in the test cell and the air line disconnected. The test cell was allowed to sit for 54 minutes at atmospheric pressure and the surface of the specimen was periodically observed for liquid penetration.

To comply with the ASTM ES 22 Test Method, three replicate specimens were tested for each type of protective clothing material submitted.

TEST CONTROLS

A negative control specimen was also included in the study to show that a negative result could be obtained consistently for some impervious materials when challenged with the φX174 bacteriophage. The negative control material used was a sterile 2 MIL polyethylene film that has consistently allowed no φX174 penetration when tested according to this procedure.

A positive control was also included in the study to show that the φX174 bacteriophage could be recovered using the assay procedure described. The positive control specimen consisted of a 0.040 µm microporous membrane that has consistently allowed φX174 penetration to occur.

Fallout plates were included for each set of specimens. The fallout plates consisted of bottom agar overlaid with top agar and *E. coli* C. The fallout plates were strategically placed on the work bench area to determine the background counts (if any) from airborne contamination.

ASSAY PROCEDURE

At the conclusion of the 54 minute test interval or when liquid penetration was observed, the drain valve was opened and the challenge drained from the test cell reservoir. The challenge collected from the test cells was assayed to determine the final concentration of the challenge suspension.

The test cell was turned into a horizontal position and a 5 mL aliquot of sterile nutrient broth with 0.01% Tween® 80 was placed onto the surface of the test specimen. The test cell was gently swirled for approximately 1 minute to ensure contact of the assay fluid with the entire viewing surface of the test specimen. The assay fluid was removed with a sterile pipette and placed into a sterile test tube. The collected fluid was then assayed for φX174.

PLAQUE ASSAY PROCEDURE

A 0.5 mL aliquot of the assay fluid was placed into triplicate tubes containing 2.5 mL of molten top agar held at 45° C.±2° C. A 102 drop aliquot of *E. coli* C was added to each tube and contents mixed and poured over the surface of bottom agar plates. After the agar solidified on a level surface, the plates were incubated at 37° C.±2° C. for 12–24 hours. The length of time depended on having the plaques large enough to count but not merging.

RESULTS

All assay titers are reported along with the challenge concentrations for each set of test specimens. All challenge concentrations were maintained at $\geq \times 10^8$ PFU/mL.

Triplicate specimens of breathable non-woven composites in accordance with the invention showed no φX174 penetration in the assay media, indicating that the specimens provided effective protection against viral penetration under the test conditions specified in this report. All test specimens are designated as "PASS" in Table 3.

The results of the fallout plates tested concurrently with each specimen indicated that the testing environment was acceptable.

The results of the negative control specimen (2 MIL polyethylene) showed some φX174 penetration in the assay fluid with an assay titer of ≈52 PFU/ml. While it is most often not the case, it is conceivable that even the 2 MIL polyethylene used as a negative control could have a flaw which would allow viral penetration. The negative control was repeated in order to show that the 2 MIL polyethylene film used as a negative control provided effective protection against viral penetration under the test conditions specified in this report and that the laboratory technician exercised proper care in performing the procedure. When repeated, the negative control specimen showed no φX174 penetration in the assay media.

The positive control specimen (0.040 μm microporous membrane) showed significant φX174 penetration on the assay plates, indicating that the specimen allowed the φX174 challenge to penetrate the specimens. This also demonstrated that the assay procedure was effective in recovering the φX174 challenge from the surface of the test specimen. Refer to Table 4 for a summary of the results of the test controls.

TABLE 2

Specimen Exposure Procedure

Procedure Pressure/Time Sequence and Retaining Screen Options

| | |
|---|---|
| A | 0 PSIG for 5 minutes, followed by 2.0 PSIG for 1 minute, followed by 0 PSIG for 54 minutes. A retaining screen is not used to support the specimen. |
| B | 0 PSIG for 5 minutes, followed by 2.0 PSIG for 1 minute, followed by 0 PSIG for 54 minutes. A retaining screen is used to support the specimen. |
| C | 0 PSIG for 5 minutes, followed by a pressure >2.0 PSIG for 1 minute, followed by 0 PSIG for 54 minutes. A retaining screen is not used to support the specimen. |
| D | 0 PSIG for 5 minutes, followed by a pressure >2.0 PSIG for 1 minute, followed by 0 PSIG for 54 minutes. A retaining screen is used to support the specimen. |

TABLE 3

Viral Penetration Results
ASTM Method ES 22
Exposure Procedure Used: A

| TEST SPECIMEN | CHALLENGE CONCENTRATION (PFU/mL) | ASSAY TITER (PFU/mL) | TEST RESULT |
|---|---|---|---|
| #1 | 2.20 × 10$^8$ | <1* | Pass |
| #2 | 2.20 × 10$^8$ | <1 | Pass |
| #3 | 2.20 × 10$^8$ | <1 | Pass |

*A value of <1 PFU/mL is reported for assay plates showing no plaques.

TABLE 4

Viral Penetration Results
ASTM Method ES 22
Exposure Procedure Used: A
Test Controls

| CONTROL SPECIMENS | CHALLENGE CONCENTRATION (PFU/mL) | ASSAY TITER (PFU/mL) | TEST RESULT |
|---|---|---|---|
| Negative Control #1 | 2.20 × 10$^8$ | ≈52 | Fail |
| Negative Control #2 | 1.08 × 10$^8$ | <1* | Pass |

TABLE 4-continued

Viral Penetration Results
ASTM Method ES 22
Exposure Procedure Used: A
Test Controls

| CONTROL SPECIMENS | CHALLENGE CONCENTRATION (PFU/mL) | ASSAY TITER (PFU/mL) | TEST RESULT |
|---|---|---|---|
| Positive Control #1 | 2.20 × 10$^8$ | ≈16 | Fail |
| Positive Control #2 | 1.08 × 10$^8$ | ≈72 | Fail |

*A value of <1 PFU/mL is reported for assay plates showing no plaques.

A second set of test were conducted with different test materials following the same procedures. Viral Penetration Test ASTM Method ES 22.

TEST CONTROLS

A control "blank" was included with each triplicate testing group. The control "blank" consisted of a sterile specimen of polyethylene placed into the test cell as previously described, however, no φX174 challenge was added to the test cell reservoir. Instead, sterile nutrient broth with 0.01% Tween® 80 was added. At the conclusion of the test period, the control "blank" was assayed as outline in the assay procedure. If the assay results of the control "blank" showed plaques, the test run was considered invalid. And under the heading of Results, the last paragraph was deleted.

Results of the second set of test are recorded in Tables 5 and 6.

TABLE 5

Viral Penetration Results
ASTM Method ES 22

| TEST SPECIMEN | CHALLENGE CONCENTRATION (PFU/mL) | ASSAY TITER (PFU/mL) | TEST RESULT |
|---|---|---|---|
| #1 | 1.16 × 10$^8$ | <1* | Pass |
| #2 | 1.16 × 10$^8$ | <1 | Pass |
| #3 | 1.16 × 10$^8$ | <1 | Pass |

*A value of <1 PFU/mL is reported for assay plates showing no plaques.

TABLE 6

Viral Penetration Results
ASTM Method ES 22
Test Controls

| CONTROL SPECIMENS | CHALLENGE CONCENTRATION (PFU/mL) | ASSAY TITER (PFU/mL) | TEST RESULT |
|---|---|---|---|
| Control Blank | N/A | <1* | Pass |
| Negative Control | 1.50 × 10$^8$ | <1 | Pass |
| Positive Control | 1.50 × 10$^8$ | 156 | Fail |

*A value of <1 PFU/mL is reported for assay plates showing no plaques.
Specimens were challenged with sterile nutrient broth with Tween ® 80 as specified in test protocol, therefore no challenge concentration was determined.

The following describes details and results (Table 7) for the microbiological viral penetration testing of protective clothing materials in accordance with the invention, which are to be used to protect against bloodborne pathogen hazards. The test procedure was adapted from the ASTM ES 22 procedure developed by the ASTM Subcommittee F23.40 on Biological Hazards. The test device used in this procedure was the ASTM F903 Chemical Penetration Cell.

The bloodborne pathogens of major concern are the hepatitis B virus (HBV), hepatitis C virus (HCV) and human immunodeficiency virus (HIV). HBV is enveloped, spherical, and 42–47 nm (nanometers) in size. HCV has no envelope, icosahedral morphology, and is 27–30 nm in size. HIV is enveloped, spherical, and is 80–110 nm in size. The blood serum concentrations of these three bloodborne pathogens ranges from less than 100 to more than 100 million IU/mL (infectious units per milliliter). The φX174 bacteriophage is one of the smallest known viruses. It has no envelope, has icosahedral morphology, and is 25–27 nm in size. The φX174 bacteriophage challenge suspension will be maintained at a concentration of at least $1.0 \times 10^8$ PFU/mL (plaque forming units/mL).

TABLE 7

Viral Penetration Results
ASTM Method ES 22

| TEST SPECIMEN | CHALLENGE CONCENTRATION (PFU/mL) | ASSAY TITER (PFU/mL) | TEST RESULT |
|---|---|---|---|
| #1 | $2.20 \times 10^8$ | <1* | Pass |
| #2 | $2.20 \times 10^8$ | <1 | Pass |
| #3 | $2.20 \times 10^8$ | <1 | Pass |

*A value of <1 PFU/mL is reported for assay plates showing no plaques.

The following describes details and results (Table 8) for the microbiological viral penetration testing of protective clothing materials in accordance with the invention, which are to be used to protect against bloodborne pathogen hazards. The test procedure was adapted from the ASTM ES 22 procedure developed by the ASTM Subcommittee F23.40 on Biological Hazards. The test device used in this procedure was the ASTM F903 Chemical Penetration Cell.

The bloodborne pathogens of major concern are the hepatitis B virus (HBV), hepatitis C virus (HCV) and human immunodeficiency virus (HIV). HBV is enveloped, spherical, and 42–47 nm (nanometers) in size. HCV has no envelope, icosahedral morphology, and is 27–30 nm in size. HIV is enveloped, spherical, and is 80–110 nm in size. The blood serum concentrations of these three bloodborne pahtogens ranges from less than 100 to more than 100 million IU/mL (infectious units per milliliter). The φX174 bacteriophage is one of the smallest known viruses. It has no envelope, has icosahedral morphology, and is 25027 nm in size. The φX174 bacteriophage challenge suspension will be maintained at a concentration of at least $1.0 \times 10^8$ PFU/mL (plaque forming units/mL).

TABLE 8

Viral Penetration Results
ASTM Method ES 22

| TEST SPECIMEN | CHALLENGE CONCENTRATION (PFU/mL) | ASSAY TITER (PFU/mL) | TEST RESULT |
|---|---|---|---|
| #1 | $1.80 \times 10^8$ | <1* | Pass |
| #2 | $1.80 \times 10^8$ | <1 | Pass |
| #3 | $1.80 \times 10^8$ | <1 | Pass |

*A value of <1 PFU/mL is reported for assay plates showing no plaques.

The following describes details and results (Table 9) for the microbiological viral penetration testing of protective clothing materials in accordance with the invention, which are to be used to protect against bloodborne patbogen hazards. The test procedure was adapted from the ASTM ES 22 procedure developed by the ASTM Subcommittee F23.40 on Biological Hazards. The test device used in this procedure was the ASTM F903 Chemical Penetration Cell.

The bloodborne pathogens of major concern are the hepatitis B virus (HBV), hepatitis C virus (HCV) and human immunodeficiency virus (HIV). HBV is enveloped, spherical, and 42–47 nm (nanometers) in size. HCV has no envelope, icosahedral morphology, and is 27–30 nm in size. HIV is enveloped, spherical, and is 80–110 nm in size. The blood serum concentrations of these three bloodborne pathogens ranges from less than 100 to more than 100 million IU/mL (infectious units per milliliter). The φX174 bacteriophage is one of the smallest known viruses. It has no envelope, has icosahedral morphology, and is 25–27 nm in size. The φX174 bacteriophage challenge suspension will be maintained at a concentration of at least $1.0 \times 10^8$ PFU/mL (plaque forming units/mL).

TABLE 9

Viral Penetration Results
ASTM Method ES 22

| TEST SPECIMEN | CHALLENGE CONCENTRATION (PFU/mL) | ASSAY TITER (PFU/mL) | TEST RESULT |
|---|---|---|---|
| #1 | $2.16 \times 10^8$ | <1* | Pass |
| #2 | $2.16 \times 10^8$ | <1 | Pass |
| #3 | $2.16 \times 10^8$ | <1 | Pass |

*A value of <1 PFU/mL is reported for assay plates showing no plaques.

What is claimed is:

1. A non-woven composite fabric comprising:

a polypropylene microporous thermoplastic film having at least one film surface thermally bonded by ultrasonic point bonding to a layer of non-woven thermoplastic materials, said film and layers being thermally bonded at multiple spaced-apart locations;

the composite fabric meeting the requirements of ASTM ES21-92 by providing a barrier to passage of biological liquid when the composite fabric is subjected to contact with synthetic blood at zero psi for 5 minutes followed by synthetic blood contact at 2 psi (13.6 kpa) for one minute followed by synthetic blood contact at zero psi for fifty-four minutes, said composite fabric exhibiting no visible penetration of synthetic blood;

the composite fabric meeting the requirements of ASTM ES22-92 by providing a barrier to viral penetration when the composite fabric is subject to contact with φX174 bacteriophage suspension at a titer of $10^8$ PFU/mL for 5 minnutes with no applied pressure, 1 minute at 13.8 kPa (2.0 PSIG), and 54 minutes with no applied pressure; and said non-woven composite fabric having a moisture or vapor transmission rate of greater than about 450 grams per square meter for twenty-four hours at about 75 degrees F and about 65% relative humidity.

2. A non-woven composite fabric according to claim 1, wherein the thermoplastic microporous film has a thermoplastic non-woven layer of the same or different materials thermally bonded to a first surface of the microporous film and a second surface of the microporous film.

3. A non-woven composite fabric according to claim 2, wherein moisture or vapor transmission is unaffected or enhanced when the non-woven layer on a first surface of the microporous film includes anti-static components and the non-woven composite fabric continues to provide a barrier to passage of biological liquids which are contacted to a non-woven layer on a second microporous film surface.

4. A non-woven composite fabric according to claim 2, wherein a first and second layer of thermoplastic non-woven materials have individual layer weights of at least 0.2 ounces per square yard to about 2.5 ounces per square yard.

5. A non-woven composite fabric according to claim 2, wherein the thermoplastic microporous film and thermoplastic non-woven materials of the layers are comprised of thermoplastic polymers.

6. A non-woven composite fabric according to claim 5, wherein said thermoplastic polymers are comprised of polyolefins or copolymers of polyolefins.

7. A non-woven composite fabric comprising:

a polypropylene microporous film having at least one film surface bonded to a layer of non-woven thermoplastic polymer, said film and layers being bonded at multiple spaced-apart locations;

said layers and microporous film being joined by ultrasonic point bonding;

said composite fabric meeting the requirements of ASTM ES22-92 by providing a barrier to passage of biological liquid as defined when the composite fabric is subjected to contact with synthetic blood at zero psi for five synthetic blood contact for fifty-four minutes;

the composite fabric meeting the requirements of ASTM ES22-92 by providing a barrier to viral penetration when the composite fabric is subject to contact with φX174 bacteriophage suspension at a titer of $10^8$ PFU/mL for 5 minutes with no applied pressure, 1 minute at 13.8 kPa (2.0 PSIG), and 54 minutes with no applied pressure; and said composite fabric exhibiting no visible penetration of the synthetic blood; said composite fabric having a moisture or vapor transmission rate of greater than about 450 grams per square meter for twenty-four hours at about 75 degrees F and about 65% relative humidity; and said woven composite fabric having a breaking strength of at least about 14 pounds.

8. A non-woven composite fabric according to claim 1, wherein the non-woven composite fabric provides a bacterial filtration efficiency test under MIL Spec. 36954C of 99% or greater.

9. A non-woven composite fabric according to claim 1, wherein the thermoplastic microporous film has a water hold-out greater than 45 pounds per square inch as measured by the Mullen burst test.

10. A non-woven composite fabric according to claim 1, wherein said thermoplastic non-woven layers, which are spun-bonded, have a grab strength in machine direction of at least 6.5 pounds to break, cross-directional of at least 5 pounds to break and an elongation value of at least 52% machine direction and at least 72% cross-direction.

11. A non-woven composite fabric according to claim 10, wherein the thermoplastic non-woven layer exposed to use environment is thicker than the layer exposed to a user.

12. A process for forming a thermally bonded non-woven composite fabric having a moisture or vapor transmission rate of greater than about 450 grams per square meter for 24 hours at about 75 degrees F and about 65 percent relative humidity, said fabric meeting the requirements of ASTM ES21-92 by providing a barrier to passage of biological liquid when the composite fabric is subjected to contact with synthetic blood at 0 psi for 5 minutes followed by synthetic blood contact at 2 psi (13.6 kpa) for 1 minute follwed by synthetic blood contact at 0 psi for 54 minutes, said composite fabric exhibiting no visible penetration of the synthetic blood; and said composite fabric having a breaking strength of at least 14 pounds per inch; the composite fabric meeting the requirements of ASTM ES22-92 by providing a barrier to viral penetration when the composite fabric is subject to contact with φX174 bacteriophage suspension at a titer of $10^8$ PFU/mL for 5 minutes with no applied pressure, 1 minute at 13.8 kPa (2.0 PSIG), and 54 minutes with no applied pressure; and comprising:

unwinding and contacting at least one continuous thermoplastic non-woven web to at least one side of a continuous polypropylene microporous film;

continuously transporting said contacted web and film through an ultrasonic point bonding zone;

thermally bonding the webs and film at multiple spaced-apart locations; said bonding having a dwell time sufficient to thermally bond while avoiding burn-through degradation of the film and webs; and forming the thermally bonded non-woven composite fabric.

13. A non-woven composite fabric according to claim 12, wherein the first and second microporous films share a single non-woven layer thermally bonded between the first microporous second surface and the second microporous first surface.

14. A non-woven composite fabric according to claim 12, wherein the first and second non-woven layer of spun-bonded thermoplastic are of different thicknesses.

15. A non-woven composite fabric according to claim 1, which exhibits a hydrostatic head of at least about 25+ pressure resistance to liquid penetration expressed in liquid column inches.

16. A non-woven composite fabric comprising:

a polypropylene microporous film having polygonal cells with average greatest dimensions of about 5 to about 30 microns and interconnecting pores between the cells having average diameters of about 0.2 to about 20 microns, the film having at least one film surface bonded to a layer of non-woven thermoplastic polymer, said film and layers being bonded at multiple spaced-apart location;

said layers and microporous film being joined by ultrasonic point bonding;

said composite fabric is subjected to contact with synthetic blood at zero psi for five minutes followed by synthetic blood contact at 2 psi for one minute followed by zero psi synthetic blood contact for fifty-four minutes;

the composite fabric providing a barrier to viral penetration when the composite fabric is subject to contact with φX174 bacteriophage suspension at a liter of $10^8$ PFU/Ml for 5 minutes with no applied pressure, 1 minute at 13.8 Kpa (2.0 PSIG), and 54 minutes with no applied pressure; and said composite fabric exhibiting no visible penetration of the synthetic blood; said composite fabric having a moisture or vapor transmission rate of greater than about 450 grams per square meter for twenty-four hours at about 75° F. and about 65% relative humidity; and said woven composite fabric having a breaking strength of at least about 14 pounds.

17. A non-woven composite fabric according to claim 16, wherein the first and second layer of thermoplastic non-woven materials bonded to a first and a second surface of the polypropylene microporous film are comprised of polypropylene and the layers have the same or different thicknesses.

18. A non-woven composite fabric according to claim 16, having at least two microporous films having individual layers of non-woven polypropylene bonded to a first and second surface of a first microporous film and a first and second surface of a second microporous film, the layers and microporous films being thermally bonded to form the non-woven composite fabric.

19. A non-woven composite fabric according to claim 17, wherein the individual non-woven layers of polypropylene bonded to surfaces of the microporous film provide a bacterial filtration efficiency test MIL Spec. 36954C of 99% or greater.

20. A non-woven composite fabric according to claim 16, wherein anti-static components are included in at least one non-woven layers.

21. A non-woven composite fabric according to claim 17, wherein the polypropylene layers are spun-bonded.

22. A non-woven composite fabric according to claim 17, wherein the first and second non-woven polypropylene layers have a basis weight of about 0.5 ounces per square yard.

23. A non-woven composite fabric according to claim 17, wherein the first non-woven polypropylene layer has a basis weight of about 0.5 ounces per square yard and the second non-woven polypropylene layer has a basis weight of about 0.9 ounces per square yard.

24. A non-woven composite fabric according to claim 16, wherein the composite fabric has been sterilized.

* * * * *